US00PP15461P3

(12) United States Plant Patent
Roose et al.

(10) Patent No.: US PP15,461 P3
(45) Date of Patent: Jan. 4, 2005

(54) MANDARIN HYBRID TREE NAMED 'TDE2'

(50) Latin Name: *Citrus reticulata*
Varietal Denomination: TDE2

(75) Inventors: Mikeal L. Roose, Riverside, CA (US); Timothy A. Williams, Riverside, CA (US); Robert K. Soost, Inverness, CA (US); James W. Cameron, Salem, OR (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/178,000

(22) Filed: Jun. 20, 2002

(65) Prior Publication Data

US 2004/0006800 P1 Jan. 8, 2004

(51) Int. Cl.[7] ..... A01H 5/00
(52) U.S. Cl. ..... Plt./202
(58) Field of Search ..... Plt./202, 201

*Primary Examiner*—Kent Bell
(74) *Attorney, Agent, or Firm*—Townsend and Townsend and Crew LLP

(57) ABSTRACT

A new mandarin hybrid called 'TDE2' is distinguished by production of fruit that combines late season maturity, large fruit size, attractive deep orange rind color and virtual absence of seeds with rich fruit flavor.

8 Drawing Sheets

Genus and species: This application is directed to a description of TDE2, which is a mandarin orange tree (*Citrus reticulata*).

BACKGROUND OF THE INVENTION

The pedigree of TDE2 is shown in FIG. 1. In 1973, pollen from Encore mandarin (unpatented) was applied to stigmas of a tetraploid (Temple×4N Dancy) hybrid (unpatented) and the pollinated flowers were bagged to prevent insect pollination. Fruits were collected in winter 1974, seeds extracted from each fruit, and each seed was planted. The chromosome number of each seedling was determined and those identified as triploid seedlings were budded onto Troyer citrange rootstock. The resulting trees were planted in the field in Riverside, Calif. in 1976. These trees were evaluated for tree vigor, bearing, and seedlings, fruit flavor, fruit color, and other fruit quality traits from bearing until 1985. Five trees were selected from the original population and repropagated by budding onto C-32 citrange, C-35 citrange, Troyer citrange, and trifoliate orange rootstocks. One of these trees, now called TDE2, was selected and further asexually propagated. Two trees of the selection now called TDE2 were planted in the field in Riverside in 1987. When they began fruiting (approximately in 1990), these two trees were evaluated for the same tree and fruit quality traits as the original trees. In 1987, the selection now called TDE2 was chosen for additional testing because it combined medium or large fruit size, low seed number, rich fruit flavor, deep orange rind and flesh color, and acceptable peelability. Budwood of this selection was tested for viruses and other pathogens by the Citrus Clonal Protection Program and virus-free bud source trees were planted at Lindcove Research and Extension Center, Exeter, Calif. in 1991.

Using this virus-free budwood source, additional trees were propagated and planted at several California locations between 1993 and 1996. These included two locations in the Coachella Valley (Thermal, 73 trees, and the Coachella Valley Agricultural Research Station-CVARS, 4 trees), Ojai (12 trees) and Santa Paula (6 trees) in Ventura Co., and Valley Center (11 trees) in San Diego Co. These trial plantings provide most of the available data on TDE2. Several different rootstocks have been used in these evaluations, mostly Carrizo citrange, C35 citrange, and Schaub rough lemon. The trees in Valley Center are top-worked Valencia orange on Troyer citrange rootstock. In general, no major effects of these rootstocks on fruit quality of TDE2 were observed, and no incompatibilities have been evident, but longevity of trees on various rootstocks is not known.

ASEXUAL REPRODUCTION

The plant known as TDE2 was first asexually propagated in 1975 when buds were collected from hybrid seedling 73-47-2 and grafted onto Troyer citrange rootstock in a greenhouse at the University of California, Riverside, Calif., U.S.A. This tree was grown in a greenhouse and in 1976 it was planted in Field 6D, Row 12, Tree 6 at the Citrus Research Center, University of California, Riverside, Calif., U.S.A. Additional asexual propagation took place in 1986 when buds were collected from field tree 6D-12,6 and grafted onto 'C32' citrange and trifoliate orange rootstocks. These trees were planted in Field 6C, Row 29, Tree positions 11 and 12 respectively in 1987.

BRIEF SUMMARY OF THE INVENTION

The present invention provides a novel mandarin hybrid having the characteristics described and illustrated herein. The hybrid, TDE2, produces fruit that combines late season maturity, large fruit size, attractive deep orange rind color and virtual absence of seeds with rich fruit flavor.

BRIEF DESCRIPTION OF THE DRAWINGS

FIG. 2 illustrates, clockwise from top left: a nine-year-old tree of TDE2 on Carrizo rootstock, fruit on tree; branching pattern; flower buds; flowers; leaves; and shoots.

FIG. 3 illustrates fruit of TDE2 sampled from nine-year-old tree on Carrizo rootstock.

FIG. 4 illustrates the solids:acid ratio of TDE2 at Santa Paula, Calif. over five years. Points plotted are means of all samples collected on a given date. Solid lines connect means for sampling dates within the same season. The dashed line is a liner regression of solids:acid on sampling date using data from all years. The regression equation and $r^2$ value are shown in each figure.

FIG. 5 illustrates the solids:acid ratio of TDE2 at Valley Center, Calif. over five years. Points plotted are means of all samples collected on a given date. Solid lines connect means for sampling dates within the same season. The dashed line is a liner regression of solids:acid on sampling date using data from all years. The regression equation and $r^2$ value are shown in each figure.

FIG. 6 illustrates the solids:acid of TDE2 at Ojai, Calif. over five years. Points plotted are means of all samples collected on a given date. Solid lines connect means for sampling dates within the same season. The dashed line is a liner regression of solids:acid on sampling date using data from all years. The regression equation and $r^2$ value are shown in each figure.

FIG. 7 illustrates the solids:acid ratio of TDE2 at Thermal, Calif. over five years. Points plotted are means of all samples collected on a given date. Solid lines connect means for sampling dates within the same season. The dashed line is a liner regression of solids:acid on sampling date using data from all years. The regression equation and $r^2$ value are shown in each figure.

FIG. 8 illustrates the solids:acid ratio of TDE2 at Coachella Valley, Calif., CVARS, over five years. Points plotted are means of all samples collected on a given date. Solid lines connect means for sampling dates within the same season. The dashed line is a liner regression of solids:acid on sampling date using data from all years. The regression equation and $r^2$ value are shown in each figure.

DETAILED DESCRIPTION OF THE INVENTION

Figure 1:
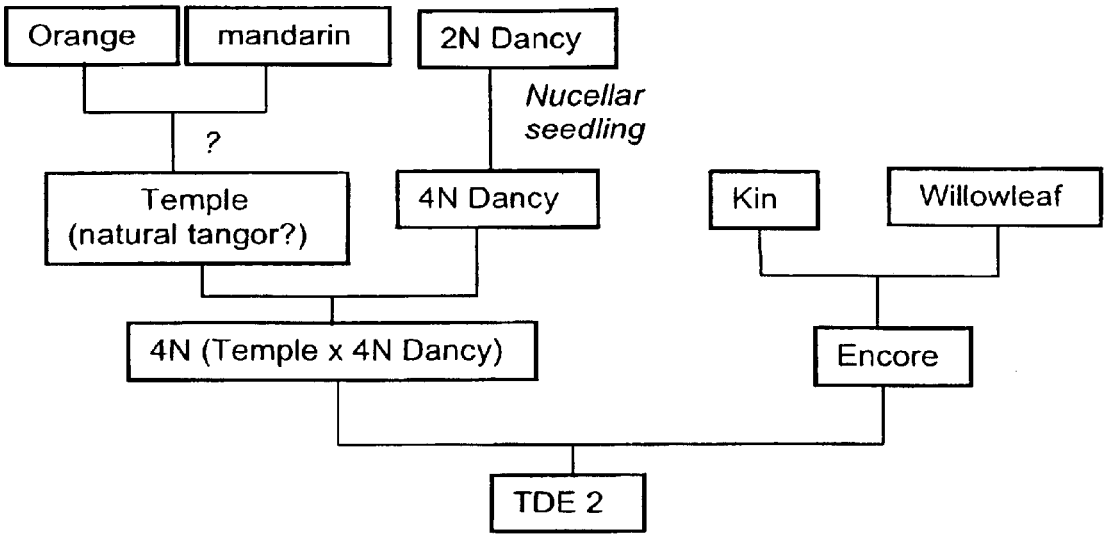
FIG. 1 illustrates the pedigree of TDE2. All cultivars are *C. reticulata* except orange, which is *C. sinensis*.

All major color code designation are by reference to The R.H.S. Colour Chart (2001) provided by The Royal Horticultural Society of Great Britain.

Eight to ten year-old trees grown in the ground were examined to prepare the description in this and the following paragraph. Tree shape is approximately sphereoid (FIG. 2), rather similar to that of orange trees. The trees have not been noted as particularly susceptible to any diseases and, based on a freeze in 1999, appeared only slightly more cold hardy than oranges of similar age. Leaves (FIG. 2) are simple, brevipetiolate (i.e., petiole shorter than leaf lamina), lanceolate, with entire or slightly sinuate margins. The petiole shape is narrow and linear in shape. In comparison with mold old-line citrus cultivars, trees of TDE2 are very thorny, with normal branches having medium length (15 mm) thorns at about 50% of the nodes, and watersprouts having long (31 mm) thorns at about 73% of nodes. Thorniness will probably decrease as the cultivar ages.

Flowers of TDE2 are typically hermaphroditic, with white (Green-White 157D, R.H.S. Colour Chart) petals and yellow (Yellow 13B, R.H.S. Colour Chart) anthers (FIG. 2). Trees flower from early April into May at most locations. Pollen is somewhat sparse, with 10% viability as estimated in an in vitro germination test. Pollen tube growth was also less vigorous than that of fertile, diploid mandarins.

The height and spread of a mature (27 years old) TDE2 tree is as follows: Tree height=6.0 m; Width=6.0 m. Trunk diameter of a 27 year old tree was 21.7 cm when measured 38 cm above the ground. Trunk color using the R.H.S. Colour Chart is Brown N200B.

Leaf characteristics of TDE2 trees are as follows:

*Leaf shape.*—Lanceolate.
*Blade length.*—82.8 mm.
*Blade width.*—43.5 mm.
*Apex description.*—Acute with weak emargination.
*Base description.*—Convex.
*Abaxial color* (*R.H.S. chart*).—Yellow Green 146A.
*Adaxial color* (*R.H.S. chart*).—Yellow Green 147A.

Petiole characteristics of TDE2 trees are as follows:

*Petiole length.*—11.2 mm.
*Petiole width.*—2.3 mm.
*Petiole color* (*R.H.S. chart*).—*Yellow Green* 147A.

If sufficient fruit was available, 10-fruit samples were collected from each location two or three times each year beginning in 1997 or 1998. Generally samples were collected from two or three trees on each sampling date. These fruit were evaluated in Riverside for a range of traits as summarized in Table 1.

TABLE 1

Fruit characteristics of TDE2 averaged over 5 locations and 4 seasons. Samples were collected from mid-January to early May at Santa Paula, Ojai, and Valley Center, and from mid-November to early April at Thermal and CVARS. "N" indicates the total number of fruit samples analyzed. Data shown are averaged over fruit from trees on various rootstocks. The trees examined for TabIe 1 ranged from 3–8 years old and were grown in the ground.

| Trait | N | Min | Max | Min | SD |
|---|---|---|---|---|---|
| Fruit height (mm) | 149 | 38.7 | 80.0 | 58.4 | 6.46 |
| Fruit width (mm) | 149 | 57.5 | 91.6 | 74.5 | 5.71 |
| Fruit height:width | 149 | 0.52 | 0.94 | 0.78 | 0.064 |
| Rind color rating[a] | 149 | 4.5 | 13.0 | 11.8 | 1.08 |
| Rind texture[b] | 149 | 2.2 | 7.5 | 3.7 | 0.68 |
| Neck rating[c] | 149 | 0 | 2.50 | 0.47 | 0.66 |
| Peelability rating[d] | 149 | 6.00 | 9.50 | 7.91 | 0.736 |
| Rind thickness (mm) | 149 | 3.00 | 6.00 | 3.86 | 0.626 |
| Seeds per fruit | 149 | 0 | 0.40 | 0.02 | 0.065 |
| Fruit weight (g) | 149 | 103.5 | 370.0 | 184.5 | 45.12 |
| Juice content (%) | 149 | 32.4 | 62.5 | 49.4 | 4.911 |
| Soluble solids (%) | 146 | 7.50 | 15.55 | 12.38 | 1.749 |
| Acid (%) | 145 | 0.62 | 2.64 | 1.22 | 0.341 |
| Solids:acid | 145 | 4.10 | 22.90 | 10.84 | 3.204 |

[a]Visual rating on a scate of 0–13; 0 = green, 13 = red-orange
[b]Visual rating on a scale of 1–8; 1 = very smooth, 8 = extremely coarse
[c]Visual rating on a scale of 0–3; 0 = no trace of neck, 3 = neck with a diameter at least 50% of fruit diameter
[d]Subjective rating of ease of peeling a single fruit; 1 = very difficult, 10 = a fruit with completely seperated rind and segments. Fruit with ratings of 7 or higher would be relatively easy to peel.

Based on this data, TDE2 fruit are oblate in shape, with little or no neck (FIG. 3). The average fruit size is large for a mandarin (classed as Mammoth by California state standards). Rind color of mature fruit is orange-red N30D (R.H.S. chart). The rind texture is variable, depending on tree age and crop. For older trees with a moderate to heavy crop, rind texture is slightly pitted, with depressed oil glands. The rind of fruit from trees with very light crops is often excessively rough or bumpy. The rind is fairly easy to peel when fruit are mature, but can be more adherent early in the season. The fruit flesh color using the R.H.S. chart is orange 28B. Flesh thickness is about 68 mm. Albedo color is Yellow-White 158C. Albedo thickness is about 2.0 mm. Adherence of rind to pulp is medium or moderate. The number of segments per fruit is 9–10. The fruit base (stalk end) is slightly concave (FIG. 3), and the apex is truncate with a slight depression in the stylar end and a small (4 mm), occasionally open stylar scar.

Important determinants of maturity date for citrus fruit are the solids:acid ratio and juice content. Using data for all years, juice content did not show a statistically significant correlation with sampling date at any of the 5 locations. This indicates that there was not generally any significant drying of fruit during the sampling period. Solids:acids ratio was significantly correlated with sampling date at all location except Santa Paula (FIG. 4). Using these regressions, the estimated dates on which fruit reached an 8:1 solids:acid was December 6 for Thermal, January 2 for Ojai, February 20 for Valley Center, and March 5 for Santa Paula. The limited data for CVARS are consistent with those for the climatically similar Thermal site.

Yield of TDE2 was evaluated from visual ratings of crop relative to tree size at each location from 1998–99 to 2001–2002. The rating scale ranged from 0 (no crop) to 5 (very heavy crop). The topworked trees in Valley Center showed the highest and most consistent crops, ranging between 3 and 4 over the 4 years studied. Crops at Ojai were also good, being 2.5 or greater in all years. At Santa Paula, crop ratings indicated alternate bearing, with average values of 2.17, 3.67, 1.17, and 3.50 from 1998–99 to 2001–2002, respectively. Trees planted at Thermal in 1994 showed similar behavior, but with lower values of 1.83, 0.50, 2.40, and 1.40, while those planted in 1996 had crops of 0, 0, 2.87, and 1.5.

As discussed above, tree fruit is set in April and May. First and last harvest dates for Riverside Calif. are estimated as February 15 and May 15. Because TDE2 is a late maturing fruit, it is likely that trees will show a fairly strong tendency to alternate bearing, and this is supported by the data for some locations.

During the 1998–99 season, fruit of TDE2 and Gold Nugget, another late season mandarin with few seeds, were harvested on April 12 from Valley Center and evaluated by a taste panel before and after storage at two different temperatures. Fruit were rated on a 9 point scale, where a score of 1 is "Dislike extremely", 5 is "Neither dislike or like", and 9 is "Like extremely". Results (Table 2) show that before storage TDE2 was preferred to Gold Nugget based on visual appearance, peelability, and taste, with good overall scores for these traits. After storage at 20.5 C for 11 days, both cultivars improved in visual appeal and peelability, but only Gold Nugget improved in taste. Storage for 12 days at 3.4 or 5.6 C followed by 7 days at 13.3 C did not greatly affect any of the ratings, but taste of both cultivars was decreased slightly in cold storage at 3.4 C. Waxed fruit were similar to unwaxed for nearly all traits. Storage at 5.6 C decreased visual appeal of TDE2 slightly while storage at 20.5 C increased visual appeal, peelability, and taste scores. Overall, these data indicate that TDE2 fruit can be stored without greatly affecting visual appeal or taste.

TABLE 2

Sensory evaluation of 'Gold Nugget' and 'TDE 2' harvested April 12, 1999 from Valley Center, CA.

| | Visual Evaluation | | | |
|---|---|---|---|---|
| | Gold Nugget −wax | Gold Nugget +wax | TDE 2 −wax | TDE 2 +wax |
| | Initial | | | |
| Mean | 4.3 | 5.0 | 6.8 | 7.0 |
| SD | 2.1 | 2.0 | 1.6 | 1.5 |

TABLE 2-continued

Sensory evaluation of 'Gold Nugget' and 'TDE 2' harvested April 12, 1999 from Valley Center, CA.

| | | | | |
|---|---|---|---|---|
| | 11 days @ 68 F. | | | |
| Mean | 5.4 | 6.2 | 7.3 | 7.9 |
| SD | 1.6 | 1.5 | 1.4 | 0.9 |
| | 12 days @ 37 F. + 7 days @ 55 F. | | | |
| Mean | 5.3 | 5.7 | 6.8 | 7.2 |
| SD. | 2.5 | 2.1 | 1.3 | 1.5 |
| | 12 days @ 41 F. + 7 days @ 55 F. | | | |
| Mean | 5.5 | 5.7 | 7.4 | 7.1 |
| SD. | 2.3 | 2.1 | 1.4 | 1.4 |
| | Peelability Evaluation | | | |
| | Gold Nugget −wax | Gold Nugget +wax | TDE 2 −wax | TDE 2 +wax |
| | Initial | | | |
| Mean | 4.6 | 4.0 | 7.0 | 6.8 |
| SD | 1.7 | 1.9 | 1.3 | 1.5 |
| | 11 days @ 68 F. | | | |
| Mean | 5.3 | 5.4 | 7.6 | 7.5 |
| SD | 2.1 | 2.2 | 1.1 | 0.8 |
| | 12 days @ 37 F. + 7 days @ 55 F. | | | |
| Mean | 5.2 | 5.6 | 7.1 | 7.2 |
| SD. | 1.7 | 1.9 | 1.6 | 1.5 |
| | 12 days @ 41 F. + 7 days @ 55 F. | | | |
| Mean | 6.1 | 5.2 | 7.4 | 7.3 |
| SD. | 1.4 | 1.7 | 1.4 | 1.5 |
| | Taste Evaluation | | | |
| | Gold Nugget −wax | Gold Nugget +wax | TDE 2 −wax | TDE 2 +wax |
| | Initial | | | |
| Mean | 5.4 | 5.3 | 6.5 | 6.8 |
| SD | 2.0 | 2.6 | 1.6 | 1.7 |
| | 11 days @ 68 F. | | | |
| Mean | 7.3 | 6.8 | 6.5 | 5.7 |
| SD | 1.7 | 1.9 | 1.7 | 1.6 |
| | 12 days @ 37 F. + 7 days @ 55 F. | | | |
| Mean | 6.1 | 6.0 | 5.8 | 6.3 |
| SD. | 1.9 | 2.4 | 1.6 | 1.5 |
| | 12 days @ 41 F. + 7 days @ 55 F. | | | |
| Mean | 6.5 | 6.6 | 6.9 | 6.5 |
| SD. | 1.6 | 1.6 | 1.4 | 1.7 |

Two siblings of TDE2, "TDE3" and "TDE4," were compared to TDE2. TDE2 is distinct from these cultivars in having the latest maturity date, the largest fruit size, a more oblate shape than TDE3, and distinct flavor. The rind color of TDE2 is usually paler orange than that of TDE4. Trees or fruit of TDE2 can be distinguished from those of other mandarins, including TDE3 and TDE4, using simple sequence repeat (SSR) DNA markers. Using TDE2 DNA as template, PCR primer set TAA15 (F=GAAAGGGTTACT TGACCAGGC, R=CTTCCCAGCTGCACAAGC) amplified a band of 185 bp, while TDE3 and TDE4 both had two bands of 185 and 200 bp. Bands amplified with TAA15 combined with those amplified with either CAC15 (F=TAA ATCTCCACTCTGCAAAAGC, R=GATAGGAAGCG TCGTAGACCC) or TAA33 (F=GGTACTGATAGTA CTGCGGCG, R=GCTAATCGCTACGTCTTCGC) distinguished TDE2 from the following cultivars: Dancy (unpatented), Temple (unpatented), Encore (unpatented), King (unpatented), Willowleaf (unpatented), Wilking (unpatented), Gold Nugget (unpatented), Pixie (unpatented), W. Murcott (unpatented), Ellendale (unpatented), Hernandina Clementine (unpatented), Fortune (unpatented), Kara (unpatented), Kinnow (unpatented), Murcott (unpatented), Nova (unpatented), and Ponkan (unpatented).

The seed (female) parent of TDE2 is a tetraploid hybrid between a 'Temple' tangor and a tetraploid tree of 'Dancy' mandarin. The tetraploid (Temple×4N Dancy) parent (referred to below as 4D-TD) was never released by the University of California and only two trees of this variety exist. TDE2 is distinct from this variety in having less than 1 seed per fruit while 4N-TD averages 10 seeds per fruit. Fruit of 4N-TD have an aspect of about 0.88, mature in December–January and hold on the tree for about 1 month, while those of TDE2 have an aspect ratio of about 0.78, mature in February and hold on the tree for 2–3 months. Fruit of 4N-TD have thicker rinds (5.5 mm) than those of TDE2. Trees of 4N-TD are somewhat smaller (3.8 m tall) than those of TDE2 (6.0 m tall).

The pollen (male) parent of TDE2 is 'Encore' mandarin. TDE2 differs from 'Encore' in that 'Encore' fruit average about 20 seeds per fruit while fruit of TDE2 have less than 1 seed per fruit. 'Encore' fruit mature in March–April, about 1 month later than those of TDE2. 'Encore' fruit always have a distinctive green or dark brown spot or blotch on the rind which is absent on TDE2 fruit. The average size of TDE2 fruit is larger than that of Encore. Encore fruit have an aspect ratio of 0.71 and much thinner rinds (2.0 mm) while those of TDE2 have an aspect ratio of 0.78 and rinds 3.5 mm thick. Encore fruit hold extremely well on the tree (4–6 months). The height of mature (35 year old) 'Encore' trees is about 4.1 m, shorter than that of mature (27 year old) TDE2 trees.

Vigor of TDE2 trees has varied greatly across locations. In the two desert locations, canopy volumes of 7-year-old trees averaged 41.1 and 28.8 $m^3$, and 5 year-old trees averaged were 9.7 $m^3$. In contrast, at the cooler Santa Paula and Ojai locations, 7-year-old trees averaged 6.3 and 6.1 $m^3$. Trees in the desert locations have averaged somewhat less crop relative to tree size, perhaps contributing to greater vegetative growth. Size of the topworked trees in Valley Center has not been measured since they are not comparable to trees in other locations, but in general the topworked trees are quite vigorous. Rootstocks had some effect on trees size. At Thermal, trees on Volkamer lemon had canopy volumes about twice that of trees on Carrizo or C35 citranges. Trees on Schaub rough lemon were usually larger than those on Carrizo or C35 citranges. No evidence of stock-scion incompatibilities was evident, but trees are still relatively young.

TDE2 can be propagated on many available citrus rootstocks by budding. Because of the high level of thorniness, great care should be taken to select budwood from upper-canopy branches having no thorns. Tree spacing in field plantings will depend on vigor of the rootstock. Trees can be grown with pollinizer cultivars such as Minneola, Valencia orange, unrelated mandarins (not Temple, Dancy, Encore or other TDE hybrids) that produce viable pollen. Maturity dates will vary with location, probably depending on the number of heat units and soil conditions.

As in some other mandarins, sprays with gibberellic acid may increase fruit set when pollinizers and/or pollinators are inadequate.

Trees are winter hardy in USDA zones 9b to 11.

What is claimed is:

1. A new and distinct variety of mandarin hybrid tree having the characteristics described and illustrated herein.

* * * * *

Figure 2. TDE3
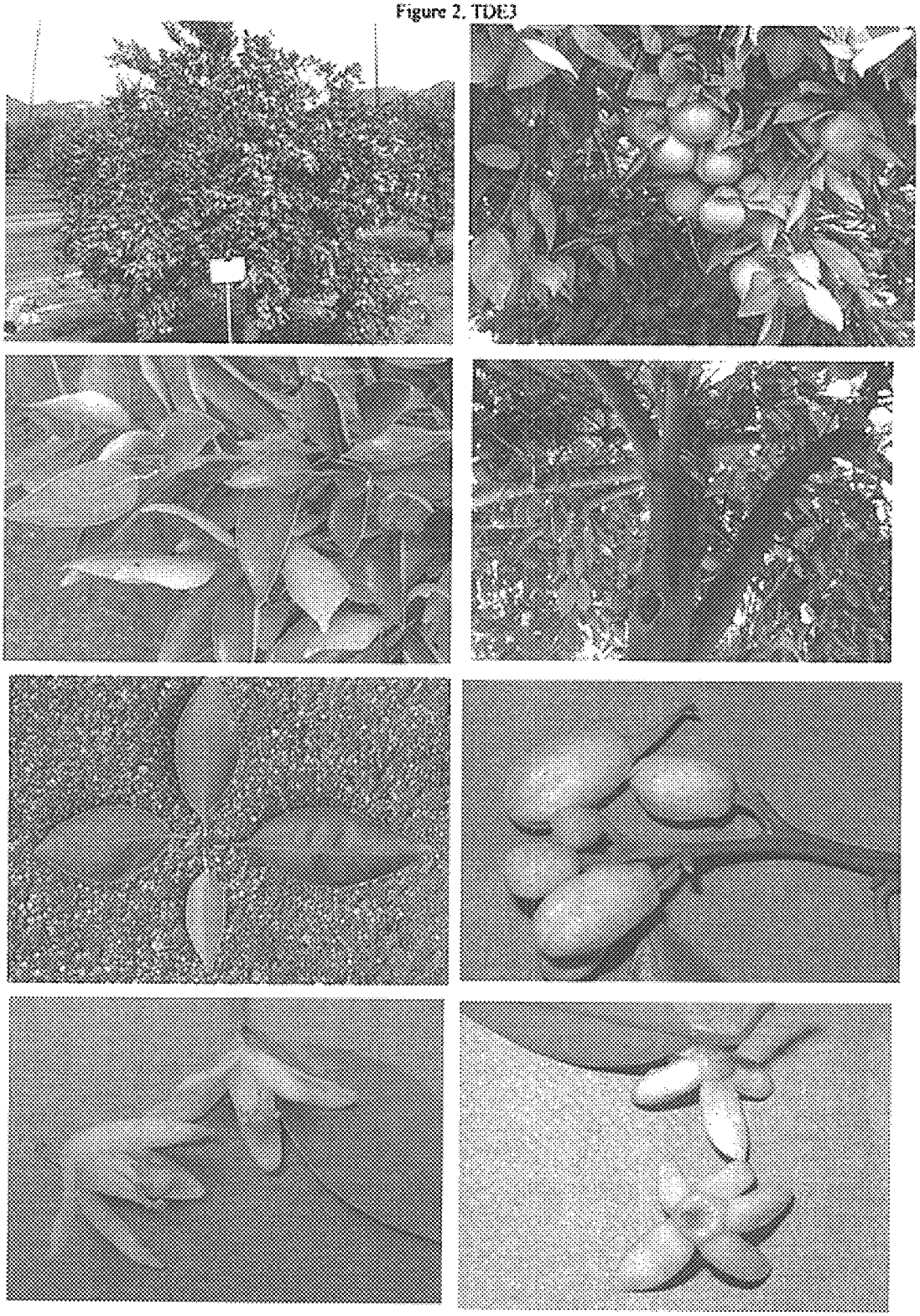

Figure 3. TDE3
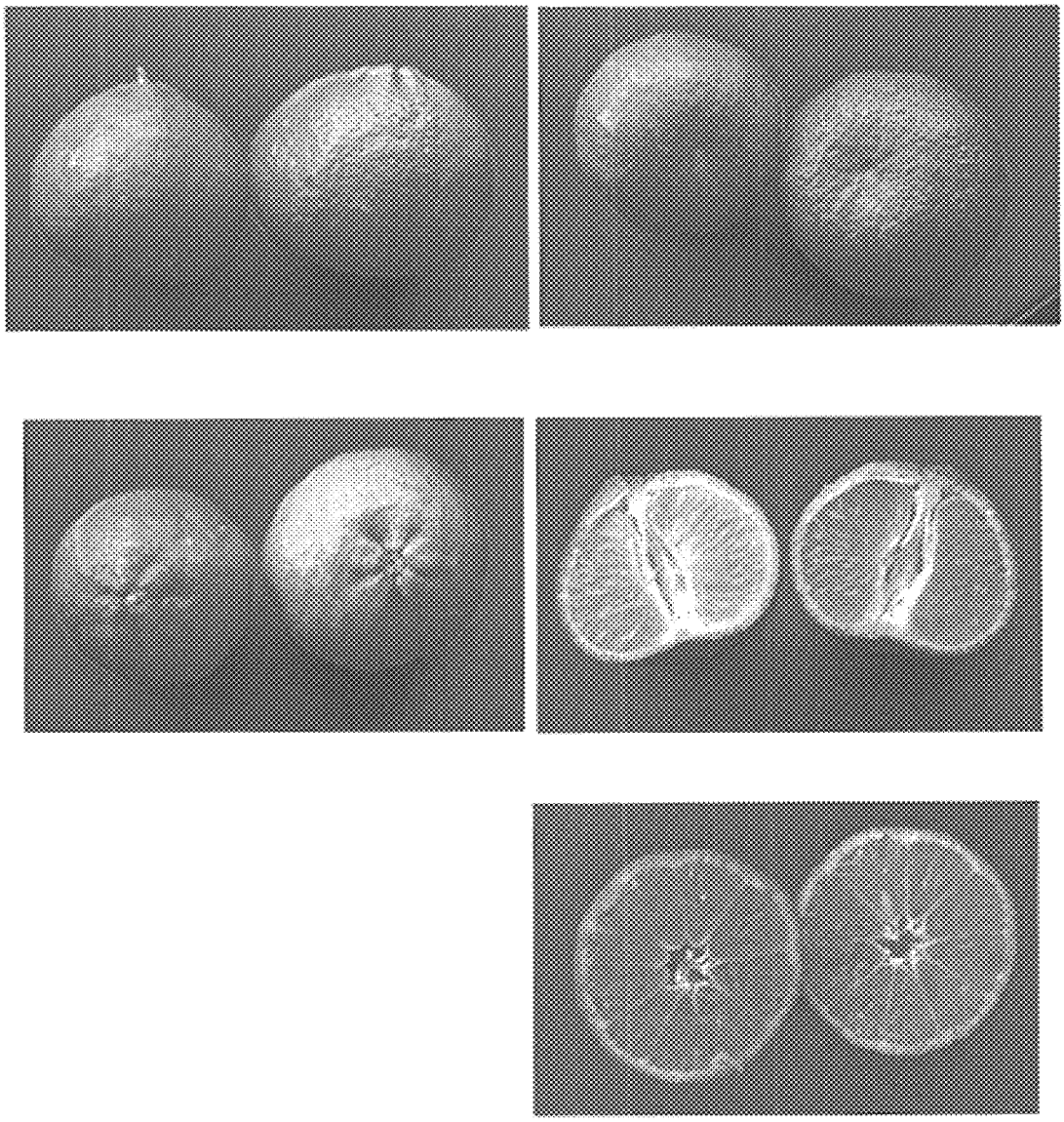

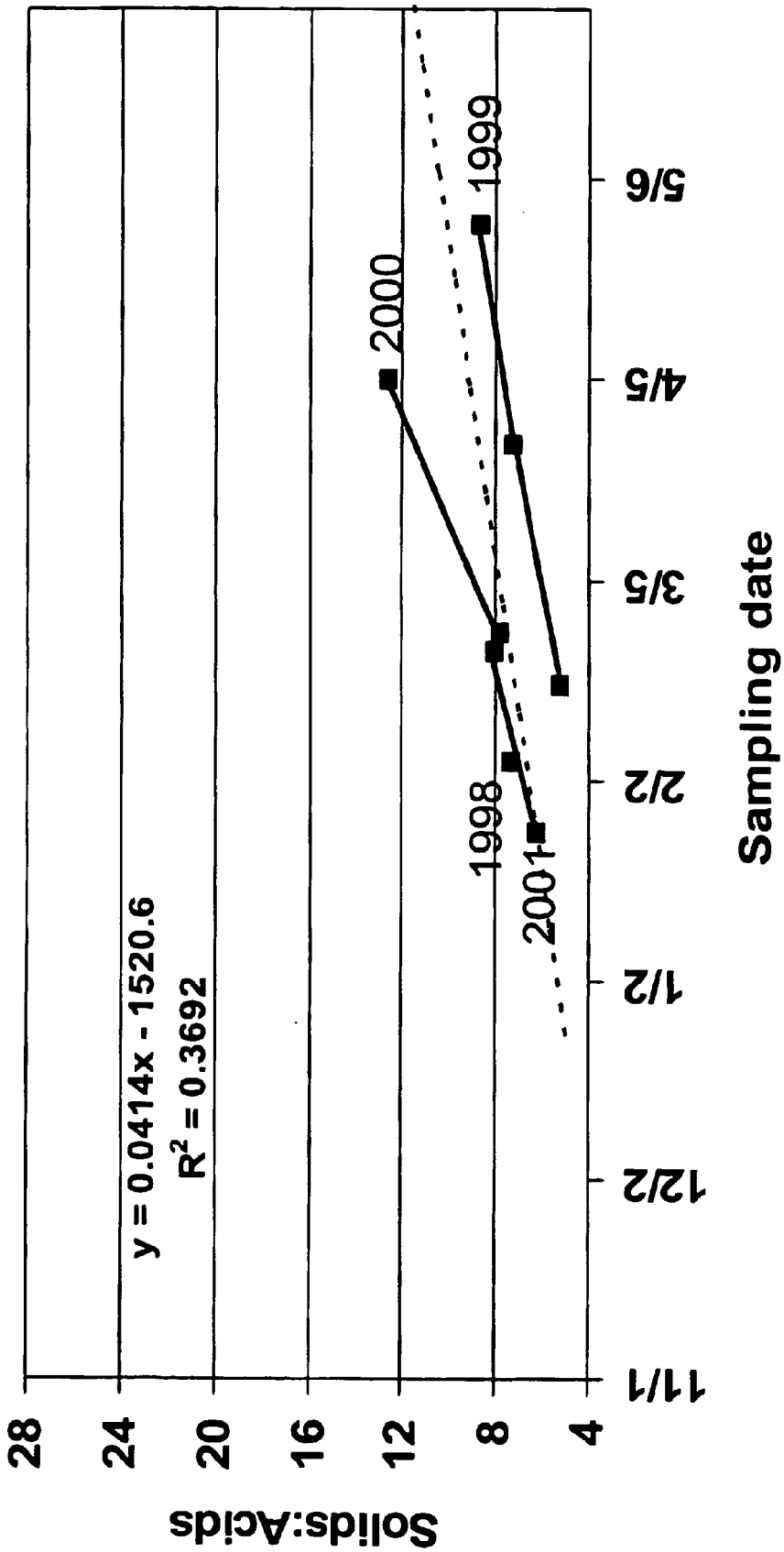
Figure 4. Solids:Acid of TDE2 at Santa Paula, CA

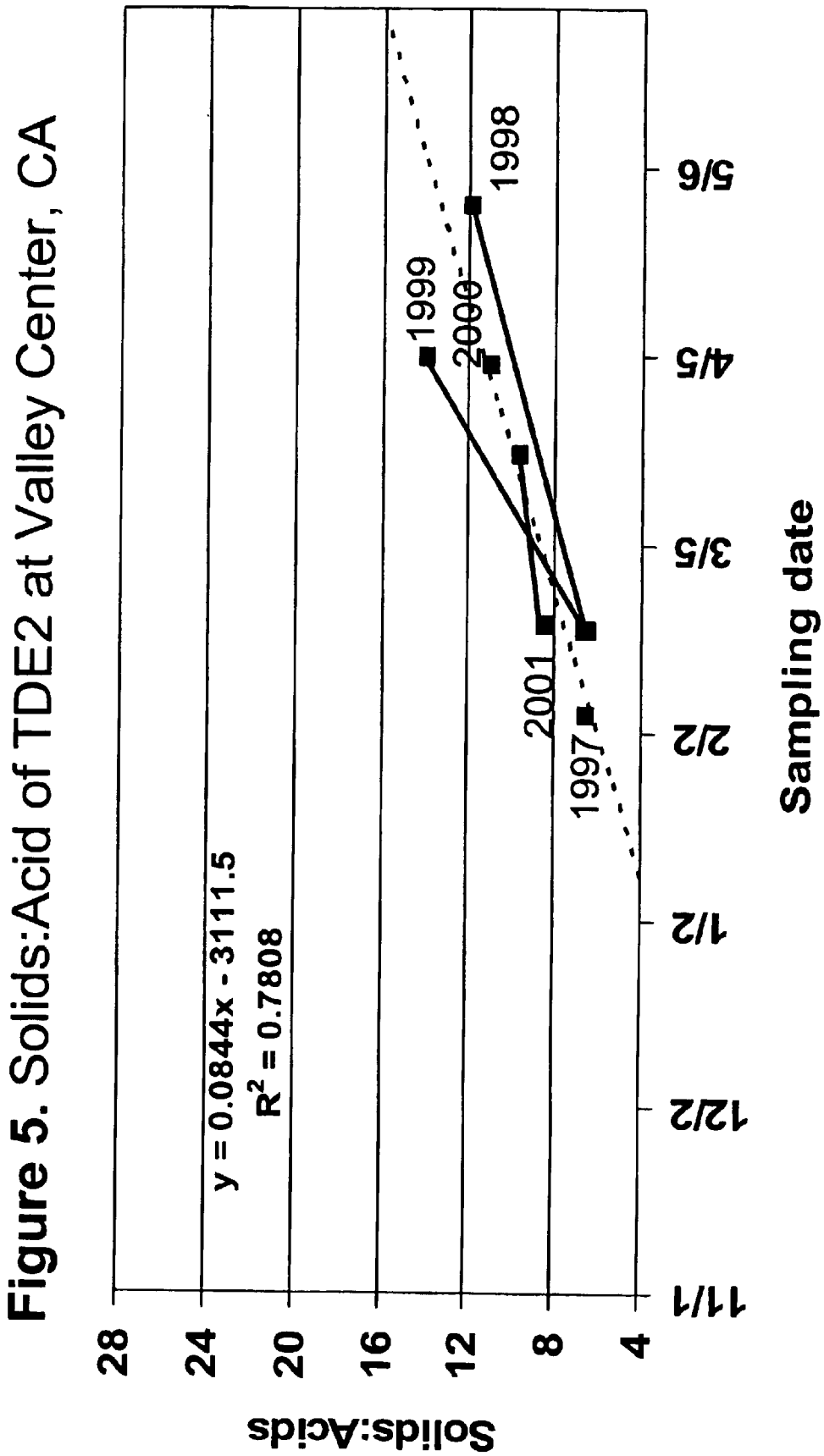
Figure 5. Solids:Acid of TDE2 at Valley Center, CA

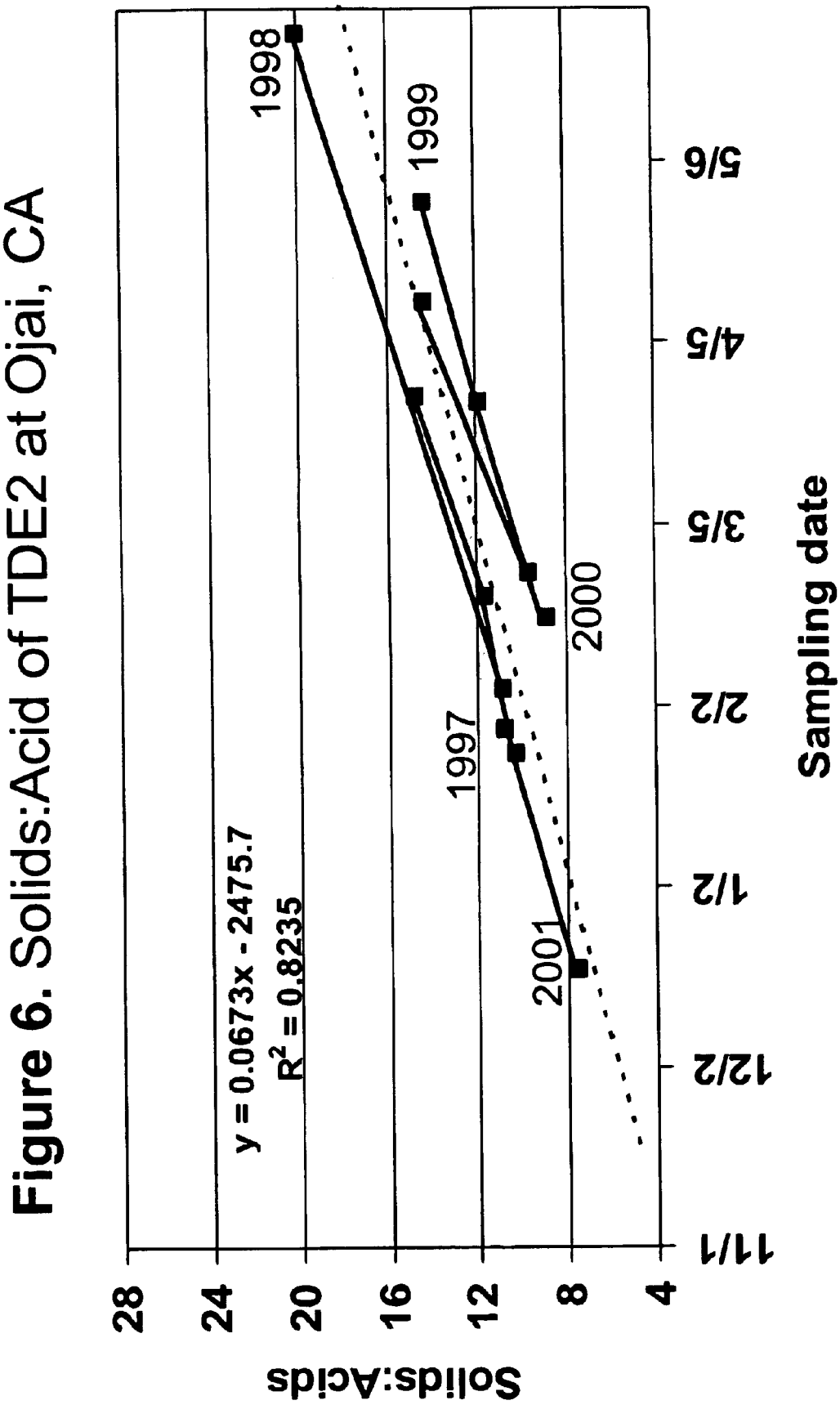
Figure 6. Solids:Acid of TDE2 at Ojai, CA
y = 0.0673x - 2475.7
R2 = 0.8235
1998
1999
1997
2000
2001
Solids:Acids
28
24
20
16
12
8
4
11/1
12/2
1/2
2/2
3/5
4/5
5/6
Sampling date

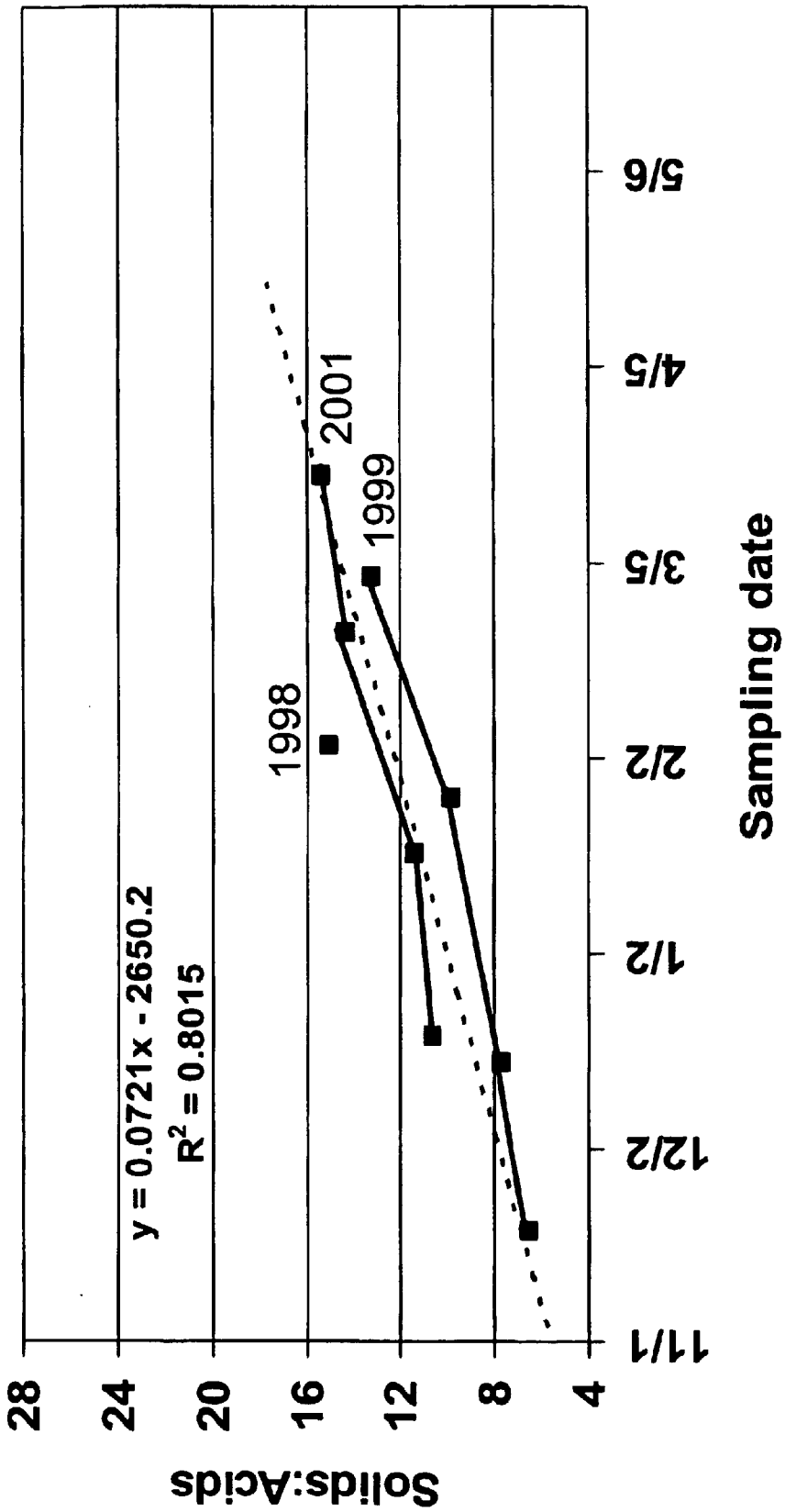
Figure 7. Solids:Acid of TDE2 at Thermal, CA

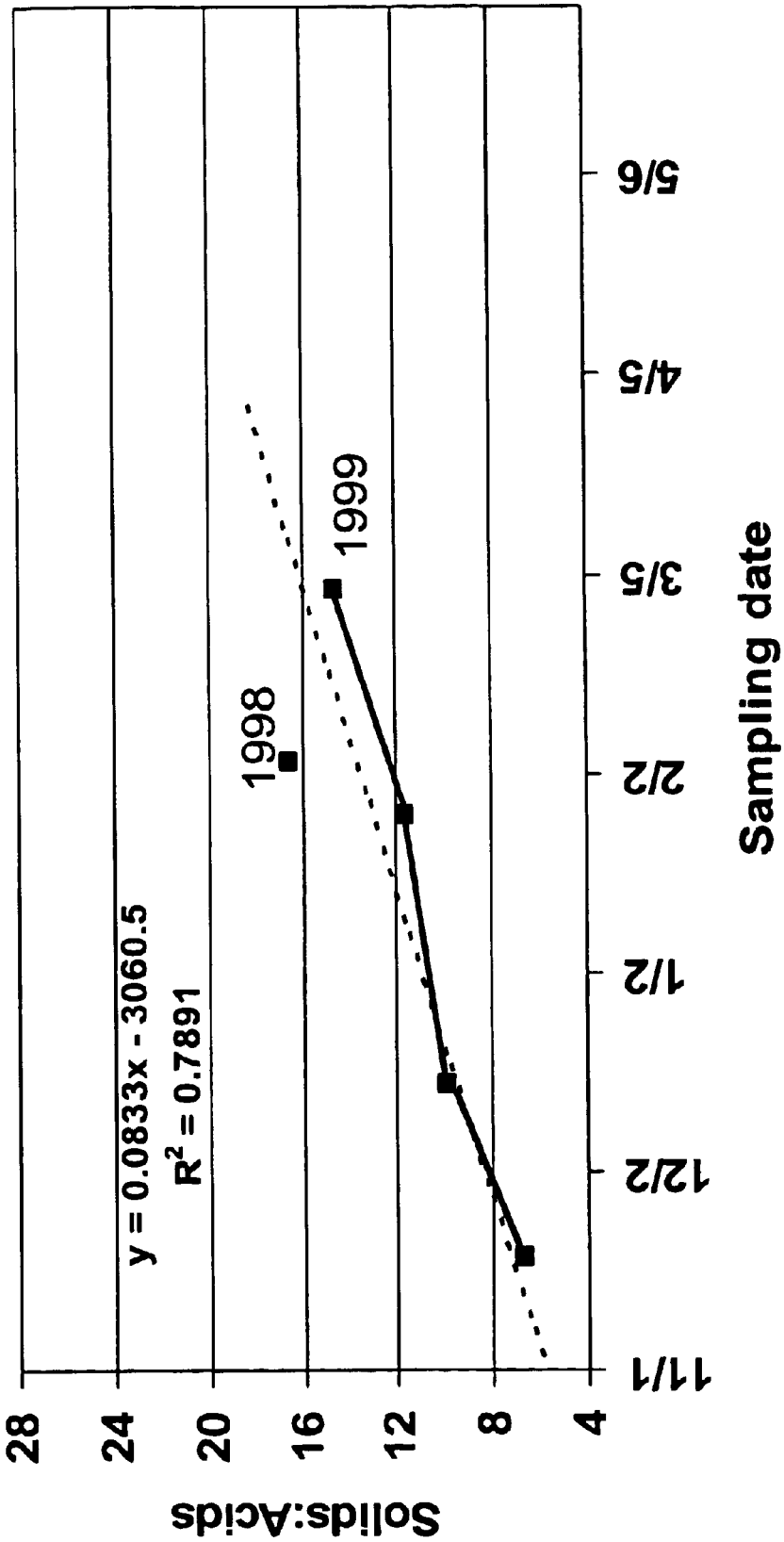
Figure 8. Solids:Acid of TDE2 at CVARS

UNITED STATES PATENT AND TRADEMARK OFFICE

CERTIFICATE OF CORRECTION

PATENT NO. : PP 15,461 P3
DATED : January 4, 2005
INVENTOR(S) : Mikeal L. Roose et al.

It is certified that error appears in the above-identified patent and that said Letters Patent is hereby corrected as shown below:

Title page,
Item [75], Inventors, change "Timothy A. Williams" to read
-- Timothy E. Williams --.

Signed and Sealed this

Thirteenth Day of September, 2005

JON W. DUDAS
*Director of the United States Patent and Trademark Office*

UNITED STATES PATENT AND TRADEMARK OFFICE

CERTIFICATE OF CORRECTION

PATENT NO. : PP 15,461 P3
APPLICATION NO. : 10/178000
DATED : January 4, 2005
INVENTOR(S) : Mikeal Roose et al.

It is certified that error appears in the above-identified patent and that said Letters Patent is hereby corrected as shown below:

Delete Drawing Sheets 2-3 and substitute therefor the Drawings Sheets, consisting of Figs 2-3, as shown on the attached pages.

Signed and Sealed this

Twenty-ninth Day of July, 2008

JON W. DUDAS
*Director of the United States Patent and Trademark Office*

Figure 2, TDE2
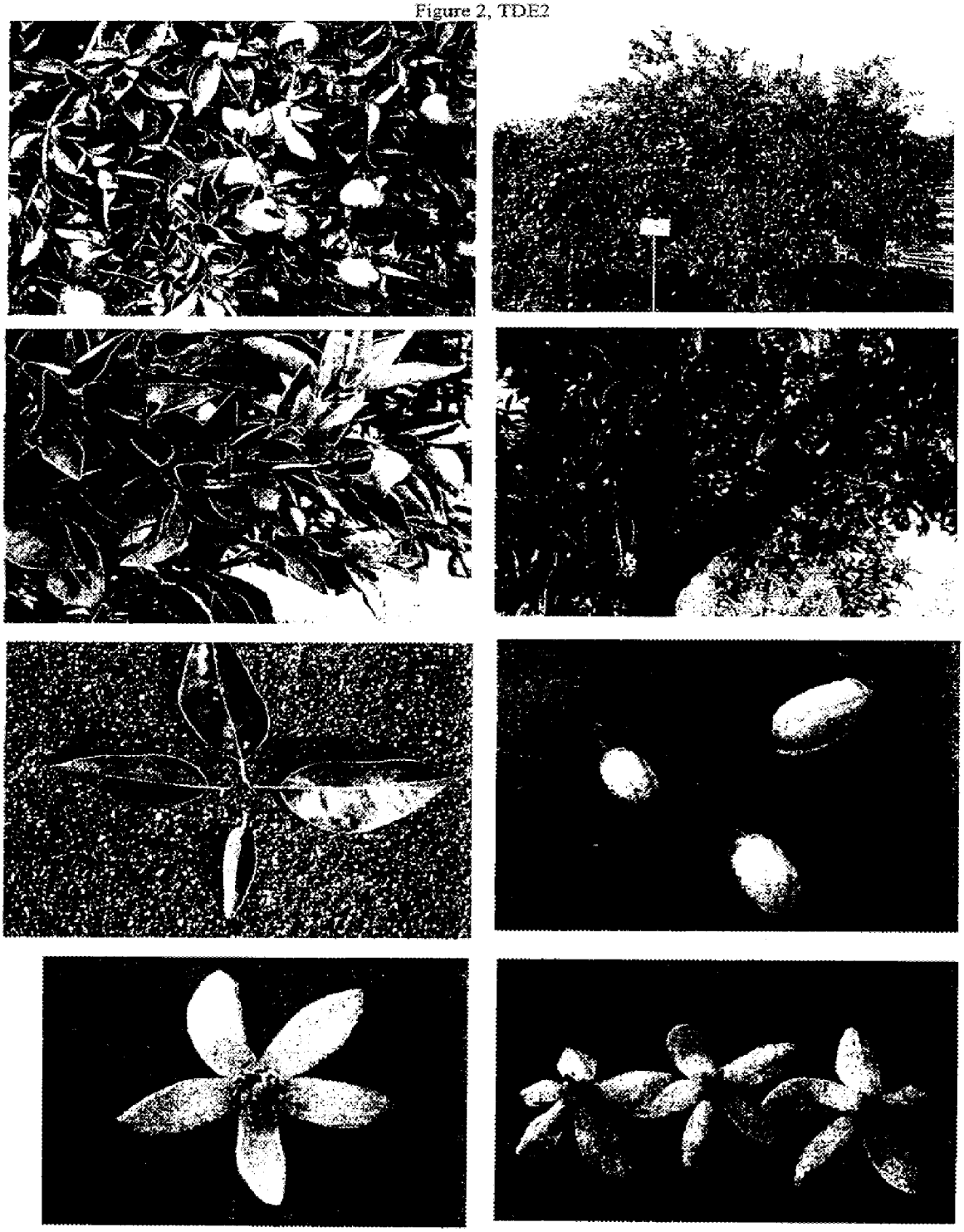

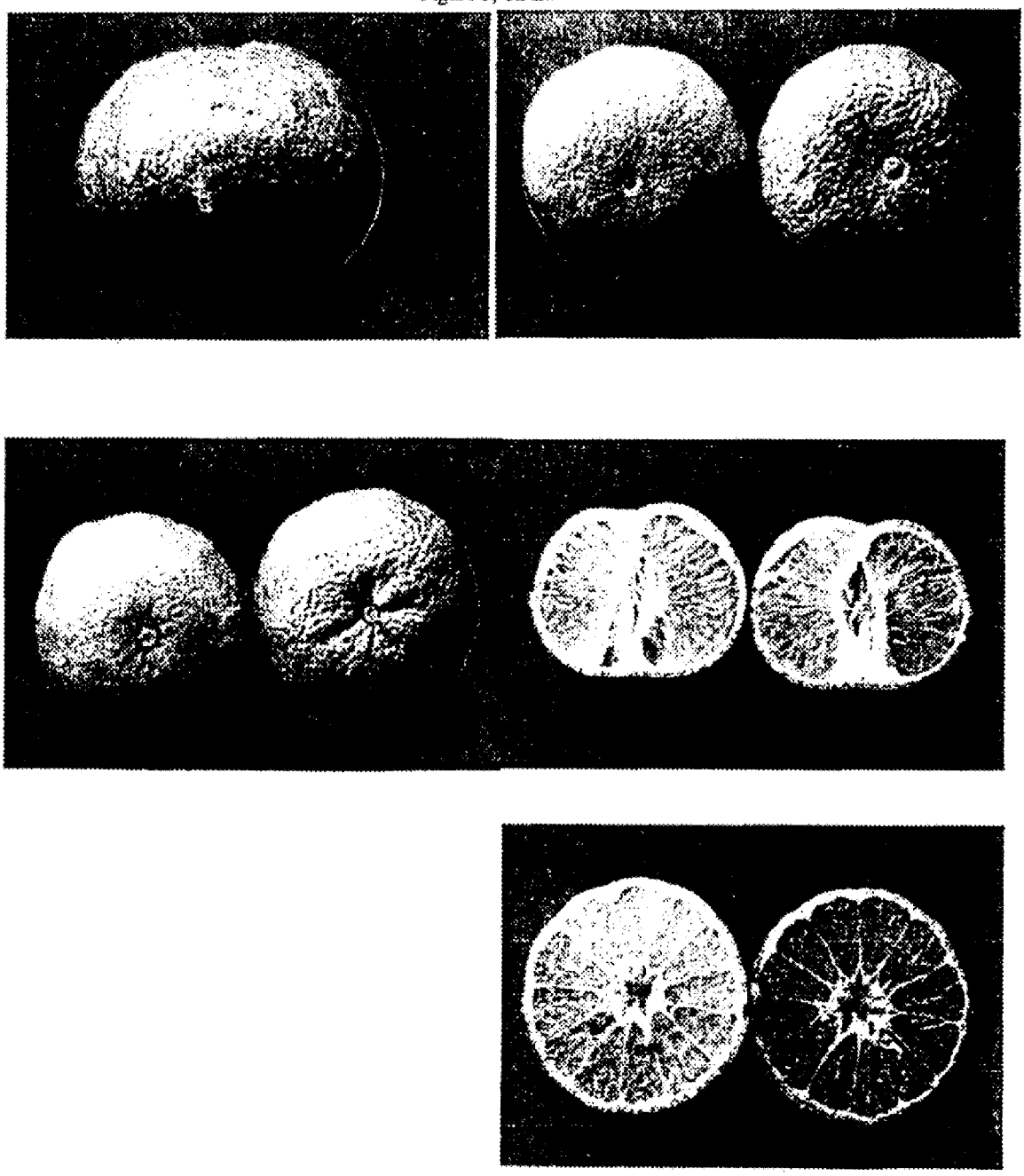

Figure 3, TDE2